(12) United States Patent
Romanowski et al.

(10) Patent No.: US 8,519,300 B2
(45) Date of Patent: Aug. 27, 2013

(54) METHOD OF LASER WELDING A HUB TO A CATHETER SHAFT

(75) Inventors: Jason Romanowski, Richfield, MN (US); Mike Sterud, Prescott, WI (US); Peter Hirshman, Golden Valley, MN (US); Anh Nguyen, Eden Prairie, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 430 days.

(21) Appl. No.: 12/938,122

(22) Filed: Nov. 2, 2010

(65) Prior Publication Data

US 2011/0139754 A1 Jun. 16, 2011

Related U.S. Application Data

(60) Provisional application No. 61/285,833, filed on Dec. 11, 2009.

(51) Int. Cl.
*B23K 26/00* (2006.01)
*A61M 25/00* (2006.01)

(52) U.S. Cl.
USPC ..................... 219/121.61; 604/523

(58) Field of Classification Search
USPC ............... 219/121.61; 604/523–527, 533
See application file for complete search history.

(56) References Cited

U.S. PATENT DOCUMENTS

| | | | |
|---|---|---|---|
| 5,380,301 A * | 1/1995 | Prichard et al. | 604/533 |
| 6,620,149 B1 * | 9/2003 | Lenz et al. | 604/524 |
| 7,001,369 B2 * | 2/2006 | Griffin et al. | 604/524 |
| 2006/0264904 A1 | 11/2006 | Kerby et al. | |
| 2007/0240817 A1 | 10/2007 | Strong et al. | |
| 2008/0108976 A1 | 5/2008 | Johnson et al. | |

FOREIGN PATENT DOCUMENTS

| WO | WO2005072787 A1 | 8/2005 |
|---|---|---|
| WO | WO2008057666 A2 | 5/2008 |

* cited by examiner

*Primary Examiner* — Sang Paik
(74) *Attorney, Agent, or Firm* — Faegre Baker Daniels LLP (57) ABSTRACT

A method of attaching a hub such as a breakaway hub to a catheter shaft includes inserting the catheter shaft into a strain relief component of the hub having one or more bosses extending radially away from the strain relief component of the hub. One or more polymeric sleeves are disposed over the strain relief component and are heat shrunk into place, followed by a laser welding process.

17 Claims, 8 Drawing Sheets

METHOD OF LASER WELDING A HUB TO A CATHETER SHAFT

CROSS-REFERENCE TO RELATED APPLICATION

This application claims the benefit under 35 U.S.C. §119 (e) to U.S. Provisional Patent Application No. 61/285,833, filed on Dec. 11, 2009, entitled "Method of Laser Welding a Hub to a Catheter Shaft," which is incorporated herein by reference in its entirety.

TECHNICAL FIELD

The present invention relates generally to medical devices such as catheters and relates more particularly to methods of manufacturing medical devices such as catheters.

BACKGROUND

A variety of medical procedures rely upon the introduction of medical instruments into a patient's vasculature so that the medical instruments may be advanced to a body location requiring diagnosis or treatment. For example, a guide catheter may be advanced through the patient's vasculature to a desired treatment site and one or more medical instruments may be advanced through the guide catheter.

It will be appreciated that depending on the nature of the patient's vasculature, the location of the treatment site, and other parameters, the desired performance characteristics of the catheter may change. Moreover, in many cases, the desired performance characteristics may conflict, such as a desire for a catheter that is both flexible yet sufficiently strong. Consequently, portions of a catheter may be made from particular materials that lend desired characteristics to an appropriate portion of the catheter.

In some cases, the particular materials used may cause difficulties in manufacture of the catheter. For example, some combinations of materials are difficult to adhesively secure together, or to weld together. There exists a need, therefore, for improved methods of manufacturing medical devices such as catheters.

SUMMARY

A hub may be attached to a catheter shaft using a mechanical entrapment to enhance welding, particularly in embodiments in which the hub and the catheter shaft are formed of materials that do not weld well.

In Example 1, a breakaway hub having an asymmetric strain relief and a boss projecting from the asymmetric strain relief may be attached to a catheter shaft. The catheter shaft is inserted into the breakaway hub such that the asymmetric strain relief extends over a proximal portion of the catheter shaft. A retainer sleeve having a slit configured to accommodate the boss therethrough is disposed over the asymmetric strain relief. A strain relief sleeve is disposed over the retainer sleeve and heat is applied to shrink the strain relief sleeve. A heat shrink tube is disposed over the strain relief sleeve and heat is applied to shrink the heat shrink tube. Laser energy is applied to secure the breakaway hub to the proximal portion of the catheter shaft and the heat shrink tube is removed. The boss projecting from the asymmetric strain relief softens and compresses while laser energy is applied.

In Example 2, the method of Example 1 in which applying laser energy further includes rotating the breakaway hub and catheter shaft while applying laser energy.

In Example 3, the method of Example 1 or Example 2 in which applying laser energy further includes translating the breakaway hub and catheter shaft while applying laser energy.

In Example 4, the method of any of Examples 1-3 further including monitoring a temperature of a surface upon which laser energy is incident upon in order to control operation of the laser.

In Example 5, the method of Example 4 in which monitoring the temperature of the surface includes applying laser energy via an infrared feedback laser.

In Example 6, the method of any of Examples 1-5 in which applying heat to shrink the strain relief sleeve comprises subjecting the strain relief sleeve to heated air.

In Example 7, the method of any of Examples 1-6 in which the breakaway hub includes a styrene-butadiene copolymer.

In Example 8, the method of any of Examples 1-7 in which the catheter shaft includes a polyether block amide having a Shore hardness of about 72D.

In Example 9, the method of any of Examples 1-8 in which the retainer sleeve includes a polyether block amide having a Shore hardness of about 55D to about 63D.

In Example 10, the method of any of Examples 1-9 in which the strain relief sleeve includes a coextruded tube having a heat-flowable polyether block amide inner layer and a cross-linked polyether block amide outer layer.

In Example 11, a hub having a proximally extending shaft portion and one or more bosses projecting from the proximally extending shaft portion may be attached to a catheter shaft. The catheter shaft is inserted into the hub such that the proximally extending shaft portion extends over a proximal portion of the catheter shaft. A retainer sleeve having a slit configured to accommodate the one or more bosses therethrough is disposed over the proximally extending shaft portion. A strain relief sleeve is shrunk down over the retainer sleeve. A heat shrink tube is shrunk down over the strain relief sleeve. The hub and catheter shaft are rotated and translated while a portion of the hub is subjected to laser energy in order to secure the hub to the proximal portion of the catheter shaft. The heat shrink tube is removed. The at least one boss projecting from the proximally extending shaft portion softens and compresses while laser energy is applied.

In Example 12, the method of Example 11 further including monitoring a temperature of a surface upon which laser energy is incident upon in order to control operation of the laser.

In Example 13, the method of Example 12 in which monitoring the temperature of the surface includes applying laser energy via an infrared feedback laser.

In Example 14, the method of any of Examples 11-13 in which the hub includes a styrene-butadiene copolymer.

In Example 15, the method of any of Examples 11-14 in which the catheter shaft includes a polyether block amide.

In Example 16, the method of any of Examples 11-15 in which the retainer sleeve includes a polyether block amide having a lower durometer value than that of the catheter shaft.

In Example 17, the method of any of Examples 11-16 in which the strain relief sleeve includes a coextruded tube having a heat-flowable inner layer and a cross-linked outer layer.

In Example 18, a hub formed of a thermoset material is attached to a catheter shaft without adhesive. A portion of the catheter shaft is inserted into the hub such that a portion of the hub extends proximally over the catheter shaft. One or more polymeric sleeves are disposed over the proximally extending portion of the hub. A mechanical attachment is formed between the catheter shaft and the proximally extending portion of the hub.

In Example 19, the method of Example 18 in which the proximally extending portion of the hub includes one or more bosses that extend radially outwardly from the proximally extending portion of the hub and that function as rivets to provide the mechanical attachment between the catheter shaft and the proximally extending portion of the hub.

In Example 20, the method of Example 19 in which forming a mechanical attachment comprises using laser energy to at least partially melt the one or more polymeric sleeves, the material forming the one or more polymeric sleeves solidifying around the one or more bosses to form the mechanical attachment.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
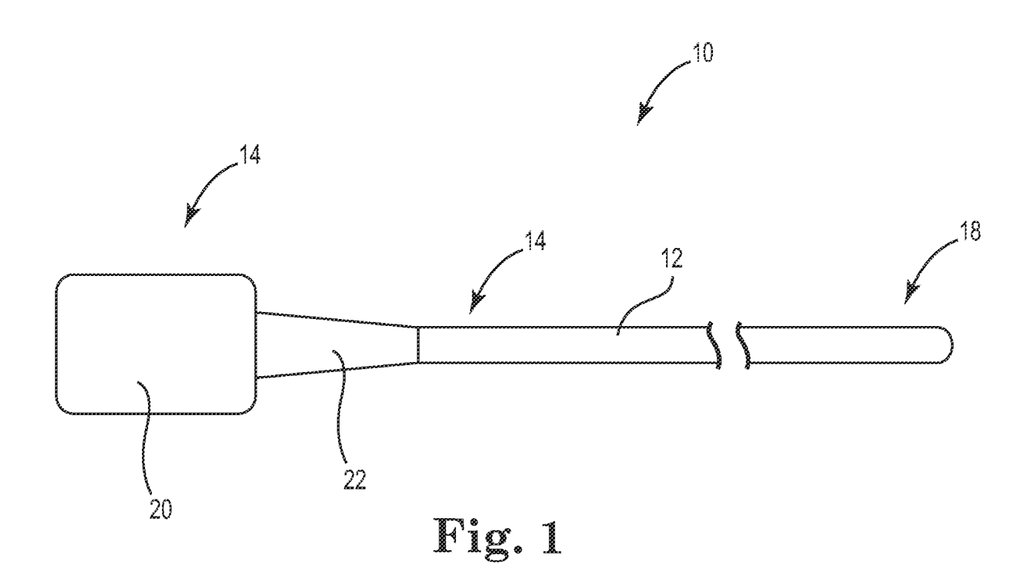
FIG. 1 is a side view of a catheter in accordance with an embodiment of the present invention.

FIG. 1 is a side view of a catheter 10 in accordance with an embodiment of the present invention. The catheter 10 may be used in any medical procedure requiring catheterization and is not intended to be limited to any particular type of catheter or catheterization procedure. The catheter 10 includes a catheter shaft 12 and a hub 14. The catheter shaft 12 has a proximal portion 16 and a distal portion 18. In some embodiments, the catheter shaft 12 may, for example, be any catheter shaft, whether known now or later developed, for use in the delivery and/or deployment of implantable medical devices (such as medical electrical leads, stents and implantable sensors) or other catheterization procedures (such as drug delivery, mapping and ablation).

The catheter shaft 12 may be formed of a single layer or two or more distinct layers that are formed of the same or different materials. In some embodiments, the catheter shaft 12 may include reinforcing materials such as metallic or polymeric braids. In some embodiments, the catheter shaft 12 may be formed of one or more thermoplastic polymers such as polytetrafluoroethylene (PTFE), ethylene tetrafluoroethylene (ETFE), fluorinated ethylene propylene (FEP), polyoxymethylene (POM, for example, DELRIN™ available from DuPont), polyether block ester, polyurethane, polypropylene (PP), polyvinylchloride (PVC), polyether-ester (for example, ARNITEL™ available from DSM Engineering Plastics), ether or ester based copolymers (for example, butylene/poly (alkylene ether) phthalate and/or polyester elastomers such as HYTREL™ available from DuPont), polyamide (for example, DURETHAN™ available from Bayer or CRISTAMID™ available from Elf Atochem), elastomeric polyamides, block polyamide/ethers, polyether block amide (PEBA, for example, available under the trade name PEBAX™, silicones, polyethylene (PE), Marlex high-density polyethylene, Marlex low-density polyethylene, linear low density polyethylene (for example REXELL™ polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR™), polysulfone, nylon, nylon-12 (such as GRILAMID™ available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof.

In some embodiments, the catheter shaft 12 or at least an outer layer thereof may be formed of a polyether block amide such as PEBAX™. A variety of PEBAX™ materials are available, having varying performance parameters such as hardness/stiffness as indicated by the durometer value of a particular PEBAX™ polymer. In some embodiments, the catheter shaft 12 or an outer layer thereof may be formed of PEBAX™ having a Shore hardness of about 72D.

In some embodiments, as illustrated, the hub 14 may include a body portion 20 and a strain relief portion 22. In some embodiments, the body portion 20 may include a lumen (not shown) in communication with one or more lumens not shown) extending through the catheter shaft 12. In some embodiments, the body portion 20 may include one or more luer fittings to accommodate attachment of fluid lines and the like. In some embodiments, the body portion 20 may be configured to act as a handle or grip and thus may include structure (not illustrated) that facilitates grasping the hub 14. In some embodiments, the hub 14 may be a breakaway or splittable hub.

In some embodiments, the strain relief portion 22 may be integrally molded with the body portion 20. In some embodiments, the strain relief portion 22 may include an inner component that is integrally molded or otherwise formed with the body portion 20 and one or more external components that help provide desired characteristics such as a flexibility/stiffness gradient between the catheter shaft 12 and the hub 14. In some embodiments, as will be explained in greater detail hereinafter, one or more of the external components may help to secure the hub 14 to the catheter shaft 12.

The hub 14 may be formed of a variety of different materials. Suitable materials include but are not limited to the materials discussed above with respect to the catheter shaft 12. In some cases, the hub 14 may be formed of a material that does not bond well, either adhesively or via welding, to the material used to form the catheter shaft 12. In some embodiments, the hub 14 is formed of a transparent material.

In some embodiments, the hub 14 may be formed of a thermoset polymer. In some embodiments, at least part of the hub 14, such as the body portion 20 and an inner component of the strain relief portion 22 may be formed of a styrene-butadiene copolymer available commercially under the K-Resin™ name.

In some embodiments, the catheter shaft 12, or at least an outer layer thereof, may be formed of a material that is difficult to secure to the hub 14 using an adhesive or by directly welding the two together. In some cases, the addition of a mechanical connection between the catheter shaft 12 and the hub 14 may be beneficial.

Figure 2:
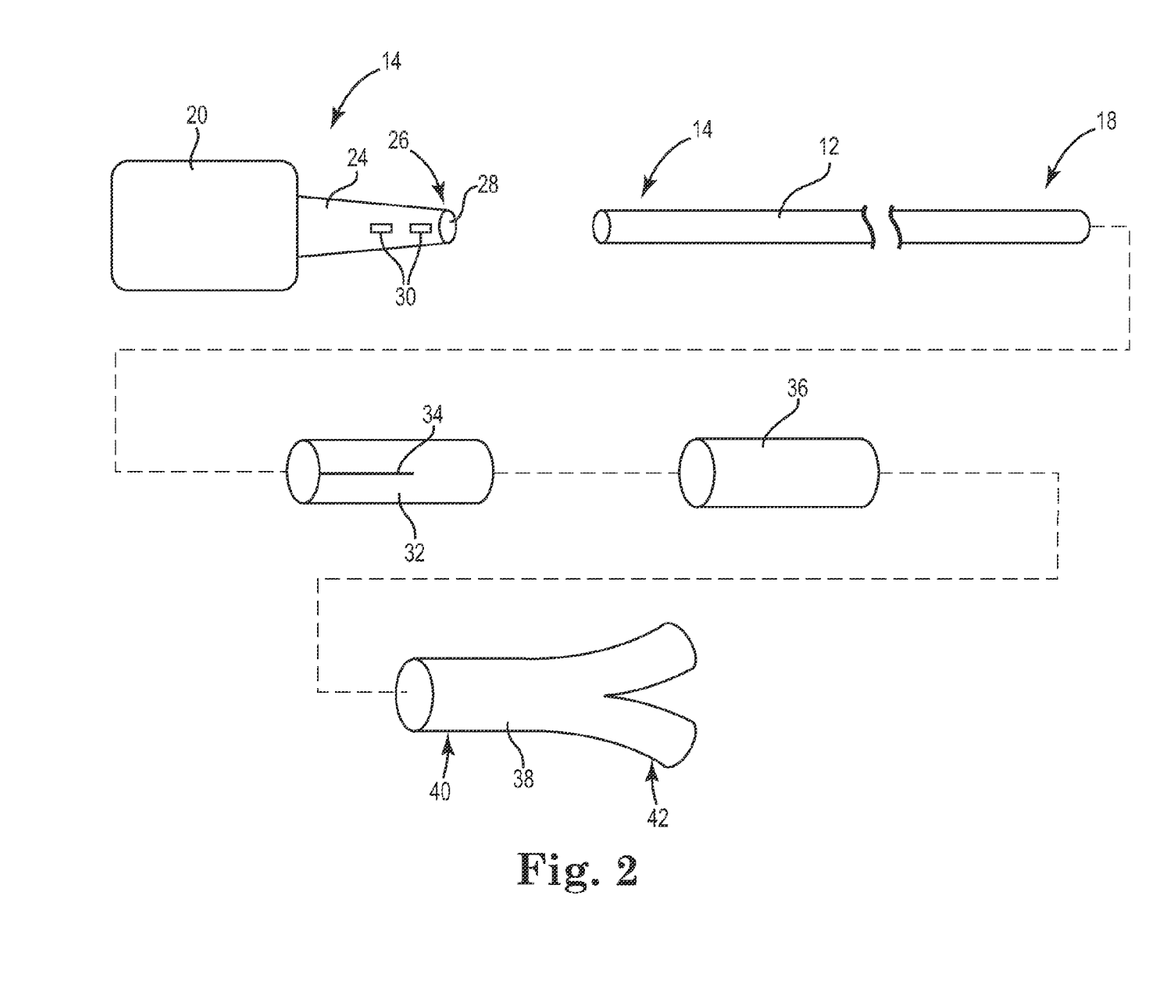
FIG. 2 is an exploded view illustrating catheter components that may be assembled to form the catheter of FIG. 1.

FIG. 2 is an exploded view illustrating components that may be combined to form the catheter 10. In the illustrated embodiment, the hub 14 includes an internal strain relief component 24 that is integrally molded or otherwise formed with the body portion 20. The internal strain relief component 24 tapers from the body portion 20 to a distal end 26 defining a lumen 28 that is configured to accommodate the proximal portion 16 of the catheter shaft 12 within the lumen 28. While the internal strain relief component 24 is illustrated as continuing in a radial direction a total of 360 degrees, in some embodiments the internal strain relief component 24 may be eccentric, particularly if the hub 14 is a breakaway or splittable hub.

In some embodiments, as illustrated, the internal strain relief component 24 may include one or more bosses 30. As will be discussed subsequently, the one or more bosses 30 help to provide a mechanical attachment between the catheter shaft 12 and the hub 14, particularly in cases where the catheter shaft 12 and the hub 14 are made of materials that are difficult to weld together. In the illustrated embodiment, two bosses 30 are visible, each having a rectangular cross-sectional profile. In some embodiments, there may be only one boss 30 or three or more bosses 30. The bosses 30 may have a square cross-sectional profile, a round cross-sectional profile or an ovoid cross-sectional profile. While the two bosses 30 are illustrated as being axially aligned, in some cases the bosses 30 may be radially scattered around the internal strain relief component 24.

Once the proximal portion 16 of the catheter shaft 12 has been inserted into the lumen 28, a retainer sleeve 32 may be advanced over the catheter shaft 12 and disposed over the internal strain relief component 24 and the proximal portion 16 of the catheter shaft 12. In some embodiments, as illustrated, the retainer sleeve 32 includes a slit 34 that opens to accommodate the bosses 30 as the retainer sleeve 32 is slid into position.

The retainer sleeve 32 may be formed of a variety of different materials such as those discussed above with respect to the catheter shaft 12. In some embodiments, the retainer sleeve 32 may be formed of a polyether block amide such as PEBAX™ having a Shore hardness value about 55D to about 63D. The length of the slit 34 may vary, depending on the geometry and relative placement of the bosses 30, but in some embodiments the slit 34 may extend about ⅔ of the length of the retainer sleeve 32.

Once the retainer sleeve 32 has been advanced into position, a heat shrinkable tube 36 may be slid over the catheter shaft 12 and disposed over the retainer sleeve 32. In some embodiments, the heat shrinkable strain relief 36 may be a composite structure having a flowable inner layer and a cross-linked outer layer. In some cases, both layers of the heat shrinkable strain relief 36 are formed of a polyether block amide such as PEBAX™. The heat shrinkable strain relief 36 may be heat shrunk down onto the retainer sleeve 32 by heating the heat shrinkable strain relief 36 to an appropriate temperature. In some embodiments, the heat shrinkable strain relief 36 is shrunk down onto the retainer sleeve 32 by subjecting the heat shrinkable strain relief 36 to heated air.

A heat shrink tube 38 having a body portion 40 and a peelable portion 42 may be advanced over the catheter shaft 12 and into position disposed over the heat shrinkable strain relief 36. The body portion 40 of the heat shrink tube 38 may be shrunk down onto the heat shrinkable strain relief 36 by applying heated air, or by any other desired technique while the peelable portion 42, extending further over the catheter shaft 12, is not heat shrunk. As a result, the peelable portion 42 provides an easy way to remove the heat shrink tube 38 after laser processing.

Once the heat shrink tube 38 has been positioned, and the body portion 40 thereof has been heat shrunk against the heat shrinkable strain relief 36, the resulting assembly can be sufficiently heated to cause the retainer sleeve 32, the heat shrinkable strain relief 36 and at least an outer layer of the proximal portion 16 of the catheter shaft 12 to melt and flow together. In some embodiments, heat may be applied using heated air or RF energy. In some embodiments, laser energy may be used.

In some embodiments, the assembly is rotated and/or translated during welding so that the assembly is evenly heated. In some embodiments, for example, the assembly may be rotated at a speed of about 200 to 250 RPM. During laser welding, the assembly is heated to a temperature that causes the retainer sleeve 32, the heat shrinkable strain relief 36 and at least an outer layer of the proximal portion 16 of the catheter shaft 12 to melt and flow together. While the internal strain relief component 24 does not melt during laser processing, the bosses 30 may soften and compress axially. Thus, the bosses 30 act as rivets and help to provide a mechanical connection between the catheter shaft 12 and the hub 14.

Figure 3:
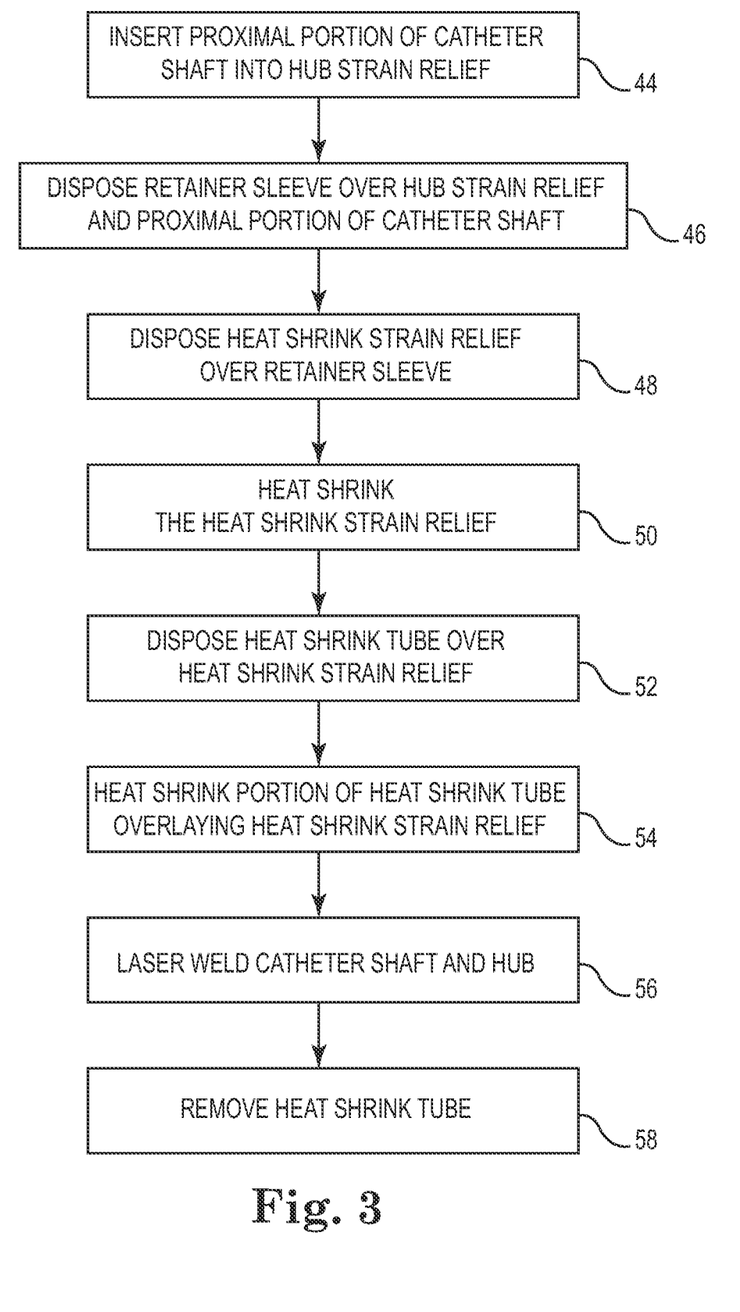
FIG. 3 is a flow diagram illustrating a method that may be used to form the catheter of FIG. 1.

FIG. 3 provides an outline of the method steps used to secure the catheter shaft 12 to the hub 14. To begin, the proximal portion 16 of the catheter shaft 12 is inserted into a hub strain relief such as the internal strain relief component 24, as generally indicated at block 44. As indicated at block 46, the retainer sleeve 32 is disposed over the hub strain relief and the proximal portion 16 of the catheter shaft 12. Next, and as indicated at block 48, the heat shrink strain relief 36 is disposed over the retainer sleeve 32 and is then heat shrunk as indicated at block 50.

The heat shrink tube 38 is disposed over the heat shrink strain relief 36, as indicated at block 52. At block 54, the heat shrink tube 38 is shrunk down onto the heat shrink strain relief 36. The catheter shaft 12 and the hub 14 are laser welded together at block 56, followed by removal of the heat shrink tube 38 at block 58. In welding together a catheter shaft and hub as referenced at block 56, it has been determined that there are unique processing considerations caused by the geometry of the parts being secured together.

For example, the strain relief portion 22 (including the internal strain relief component 24) is tapered, meaning that a laser-to-work piece distance is non-uniform. In some cases, as will be discussed subsequently, the internal strain relief component 24 may be eccentric, providing an uneven mass distribution. Compared to other welding such as welding a balloon onto a catheter shaft, the welding process described herein has a much larger processing length. While welding a balloon waist to a catheter shaft may, for example, involve a welding length of about 2 to 4 millimeters, the welding described herein may involve a welding length of about 32 millimeters. In some embodiments, this distance may vary, depending on the geometry of the pieces being secured together.

Figure 4:
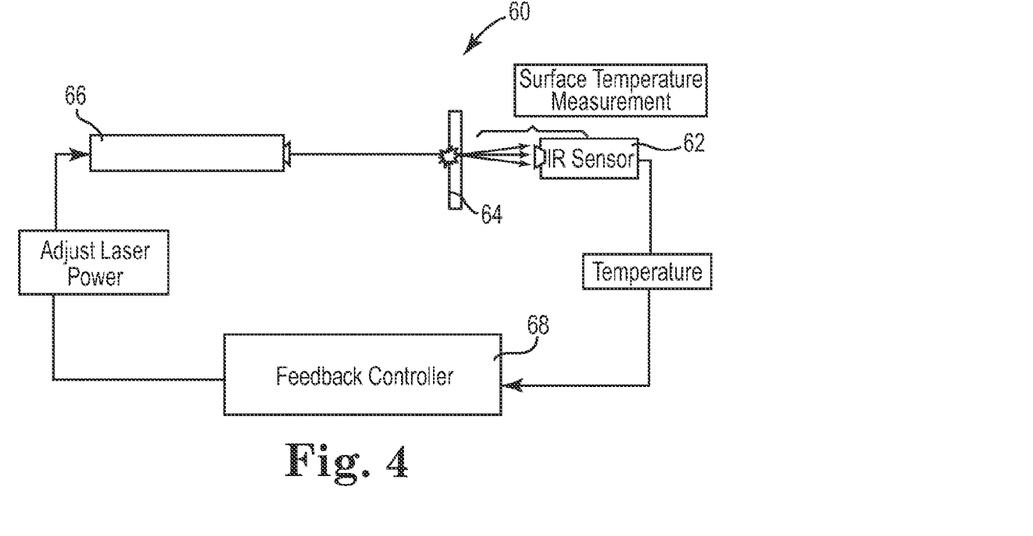
FIG. 4 is a schematic illustration of an embodiment of a laser welding system that may be used in the method of FIG. 3.

To accommodate the unique requirements of the invention, a feedback laser system may be used in which the laser is controlled at least in part based upon the temperature of the work piece. FIG. 4 is a schematic illustration of a feedback laser system 60 that may be used in the laser welding process referenced at block 56 of FIG. 3. In this system, an IR (infrared) sensor 62 monitors a surface temperature of the work piece 64 (a combination of the components individually illustrated in FIG. 2) while a laser 66 provides a laser beam that impinges on the work piece 64. In the illustrated embodiment, the laser 66 is a CO2 laser. In some embodiments, other lasers may be used. In some embodiments, other temperature sensors may be used.

The IR sensor 62 provides temperature information to a controller 68 (which may be manifested in software running on a personal computer). While the controller 68 is illustrated as a PID (proportional-integral-derivative) controller, in some embodiments other control strategies may be used. The controller 68 regulates the intensity of the laser 66 in accordance with a preprogrammed set point temperature (and/or recipe) to achieve and maintain the set point temperature while compensating for the geometric issues referenced above.

Figure 5:
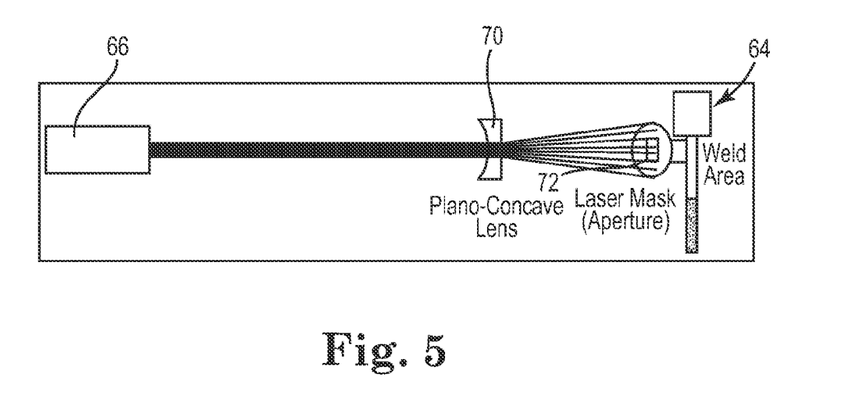
FIG. 5 is a schematic illustration of a portion of the laser welding system of FIG. 4.

As illustrated in FIG. 5, a plano-concave lens 70 may be used to provide a more diffuse laser beam, thereby permitting the laser beam to simultaneously impinge on a relatively larger area. A laser mask 72 may be used to limit laser beam impingement on a particular region or section of the work piece 64. While other laser welding processes such as balloon welding may use a laser mask 72 having a 2 millimeter by 6 millimeter opening, it has been determined that a larger opening of 4 millimeter by 6 millimeter is more appropriate for the welding processes discussed herein.

Figure 6:
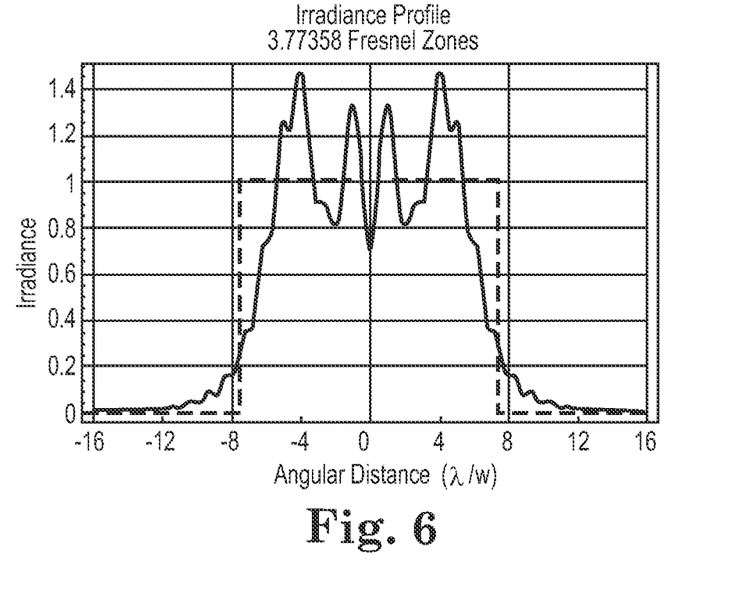
FIGS. 6 and 7 illustrate a performance advantage of the laser welding system of FIG. 4.
Figure 7:
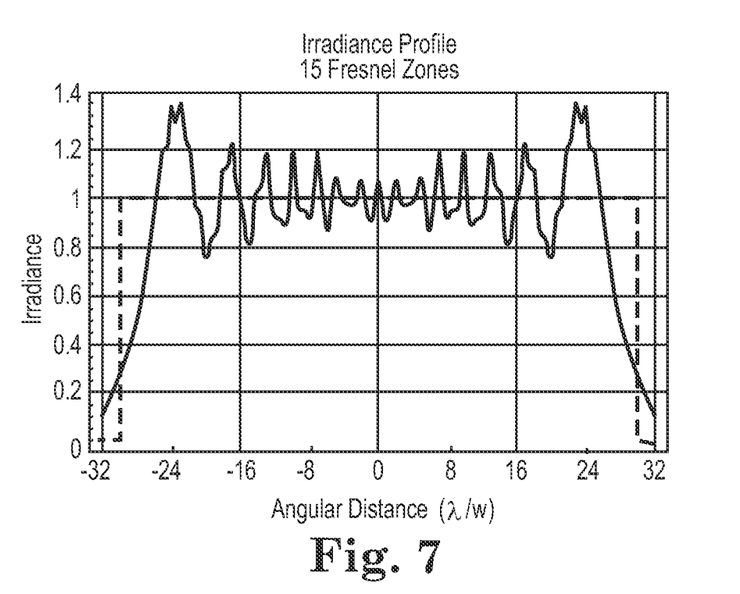

While it was determined that the larger laser mask opening increases the speed at which the welding can be achieved, it was surprisingly discovered that the larger laser mask opening provided for a more uniform beam profile. This can be seen by comparing the irradiance profile in FIG. 6 (2×6 mask opening) with that of FIG. 7 (4×6 mask opening). It has been determined that the more uniform beam profile provides unexpected manufacturing advantages.

Figure 8:
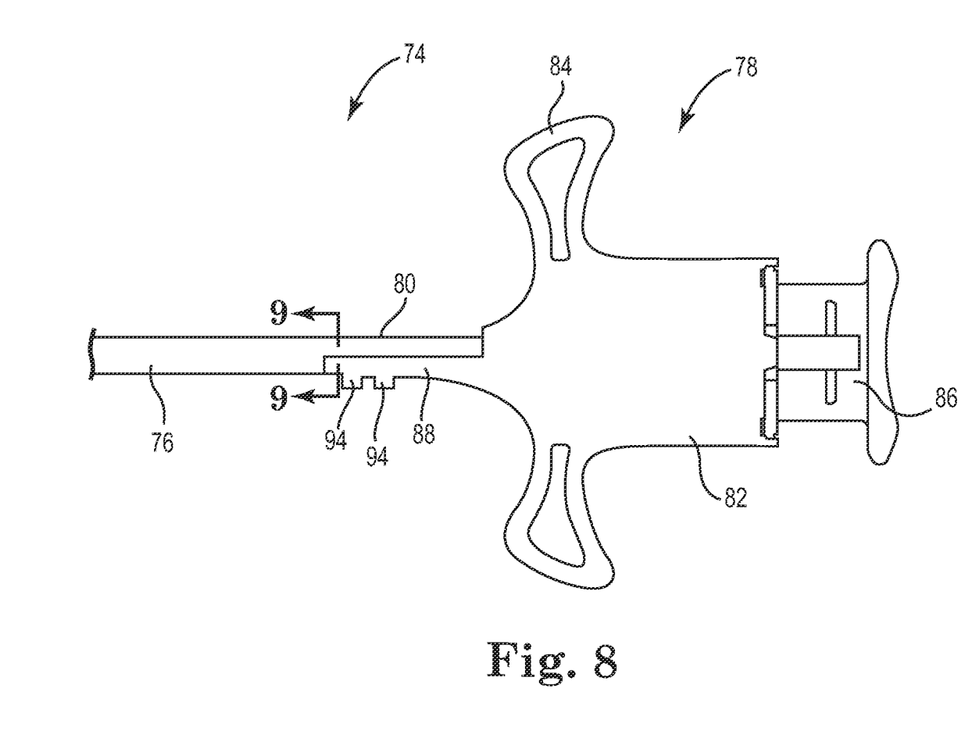
FIG. 8 is a side view of a catheter assembly in accordance with an embodiment of the invention.
Figure 9:
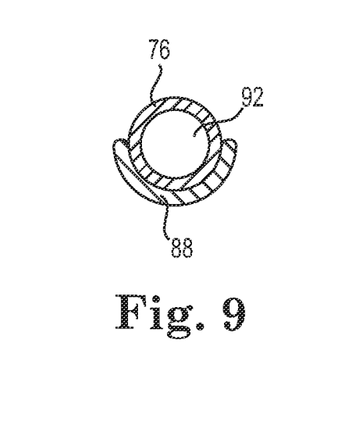
FIG. 9 is a cross-sectional view of a portion of the catheter assembly of FIG. 8.
Figure 10:
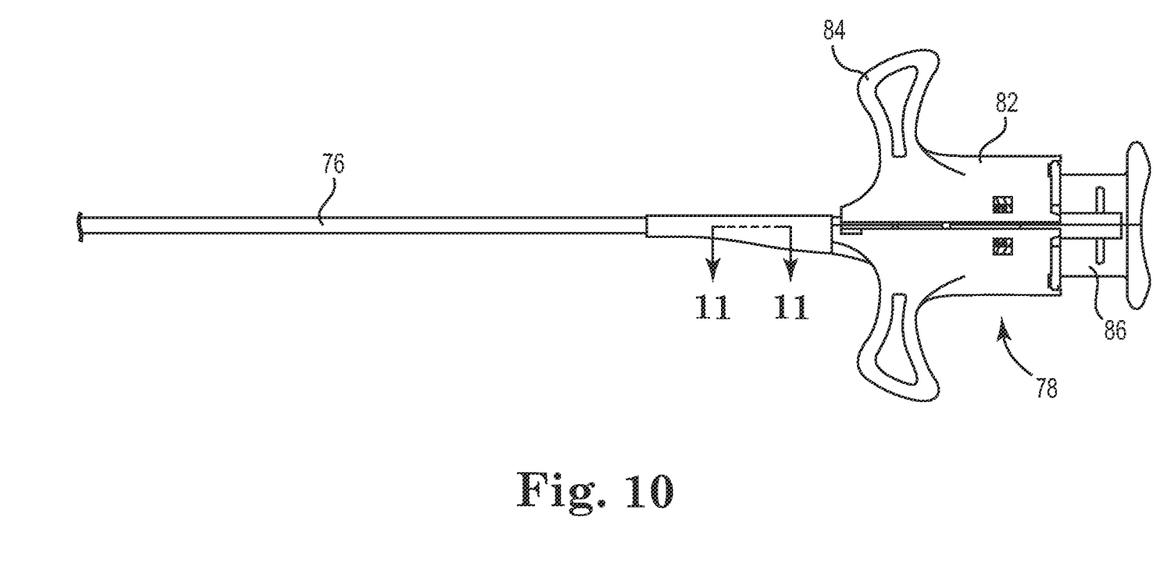
FIG. 10 is a side view of the catheter assembly of FIG. 8, showing part of the assembly process.

FIGS. 8 through 10 provide an illustrative but non-limiting example of a catheter that can be formed using the materials and methods discussed above. FIG. 8 is a side elevation view of a catheter assembly 74 that may be manufactured using the methods described herein.

The catheter assembly 74 includes a catheter shaft 76 and a hub 78. As illustrated, the catheter shaft 76 includes a proximal portion 80. The catheter shaft 76 may be formed of any suitable materials, including those discussed above with respect to the catheter shaft 12. In some embodiments, the catheter shaft 76 or at least an outer layer thereof may be formed of a polyether block amide such as that available commercially under the PEBAX™ name. In some embodiments, the catheter shaft 76 or an outermost layer thereof may be formed of PEBAX™ having a Shore hardness value of about 72D.

In some embodiments, as illustrated and as described in greater detail hereinafter, the hub 78 may be a breakable or splittable hemostasis hub. The hub 78 may be formed of any suitable material such as those discussed above with respect to the hub 14, including thermoset materials. In some embodiments, the hub 78 may be formed of a styrene-butadiene copolymer such as that available commercially under the K-RESIN™ name.

In some embodiments, the hub 78 may, as illustrated, include a body portion 82 and a handle portion 84 that is molded into or otherwise attached to the body portion 82. The hub 78 may include an actuator portion 86 that is slidably disposed within the body portion 82. In some embodiments, the hub 78 may be a hemostasis hub and thus may include an internal seal that seals the interior of the catheter shaft 76 from a lumen extending through the hub 78. In some embodiments, the internal seal may be penetrated by moving the actuator portion 86 inwards (from its illustrated position). Further details regarding the construction and operation of the hub 78 may be found in U.S. Patent Publication No. 2008/0108976 entitled "BREAKAWAY HEMOSTASIS HUB", which application is hereby incorporated by reference herein in its entirety.

A strain relief component 88 extends proximally from the body portion 82. In contrast to the internal strain relief component 24 discussed above, the strain relief component 88 is asymmetric. In some embodiments, the strain relief component 88 may be considered as having a radial cross-sectional profile that is semicircular. This is illustrated in FIG. 9, in which the catheter shaft 76 may be seen as defining an internal lumen 92.

In some embodiments, as illustrated, the strain relief component 88 may include one or more bosses 94 that help to provide a mechanical attachment between the catheter shaft 76 and the hub 78, particularly in cases where the catheter shaft 76 and the hub 78 are made of materials that are difficult to weld together. In the illustrated embodiment, two bosses 94 are visible, each having a rectangular cross-sectional profile. In some embodiments, there may be only one boss 94 or three or more bosses 94. The bosses 94 may have a square cross-sectional profile, a round cross-sectional profile or an ovoid cross-sectional profile. While the two bosses 94 are illustrated as being aligned, in some cases the bosses 94 may be radially scattered around the strain relief component 88.

The catheter shaft 76 may be secured to the hub 78 in a manner similar to that shown above with respect to FIG. 2. As seen in FIG. 10, several additional elements have been added to the catheter assembly 74. In FIG. 10, a retainer sleeve has been disposed over the strain relief component 88 and the catheter shaft 76. A heat shrink strain relief has been disposed over the retainer sleeve but has not yet been shrunk down. This can be seen in FIG. 11, which is a partial cross-section taken through the strain relief component 88.

Figure 11:
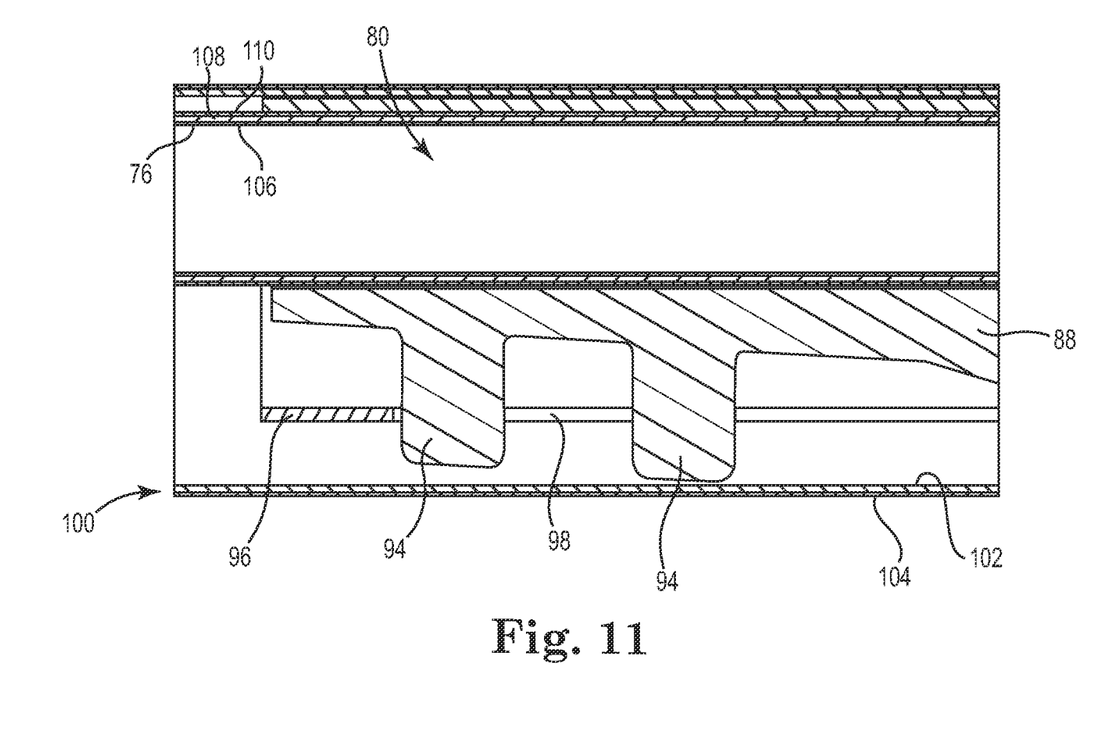
FIG. 11 is a partial cross-sectional view of FIG. 9.

In FIG. 11, only a distal portion of the strain relief component 88 is illustrated, including the bosses 94. A retainer sleeve 96 having a slit 98 defined within the retainer sleeve 96 has been advanced over the proximal portion 80 of the catheter shaft 76 and the retainer sleeve 96. A heat shrink strain relief 100 has been disposed over the retainer sleeve 96. In some embodiments, as illustrated, the heat shrink strain relief 100 includes an inner layer 102 and an outer layer 104. In some embodiments, the inner layer 102 may be a flowable PEBAX™ material while the outer layer 104 may be a cross-linked PEBAX™ material.

In the illustrated embodiment, the catheter shaft 76 includes an inner layer 106, an intermediate layer 108 and an outer layer 110. In some cases, the outer layer 110 is formed of a polyether block amide such as PEBAX™. In some embodiments, the inner layer 106 may be formed of a lubricious material such as polytetrafluoroethylene (PTFE) or polyethylene. In some embodiments, the intermediate layer 108 may be a polymeric material or a reinforcing member such as a braid. The assembly shown in FIGS. 9 and 10 may be processed in a similar manner to that described above with respect to FIG. 2. The heat shrink strain relief 100 may be heat shrunk prior to a laser welding process.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of attaching a breakaway hub to a catheter shaft, the breakaway hub having an asymmetric strain relief and a boss projecting from the asymmetric strain relief, the catheter shaft including a proximal portion, the method comprising steps of:
    inserting the catheter shaft into the breakaway hub such that the asymmetric strain relief extends over the proximal portion of the catheter shaft;
    disposing a retainer sleeve over the asymmetric strain relief, the retainer sleeve including a slit configured to accommodate the boss therethrough;
    disposing a strain relief sleeve over the retainer sleeve;
    applying heat to shrink the strain relief sleeve;
    disposing a heat shrink tube over the strain relief sleeve;
    applying heat to shrink the heat shrink tube;
    applying laser energy to secure the breakaway hub to the proximal portion of the catheter shaft; and
    removing the heat shrink tube;
    wherein the boss projecting from the asymmetric strain relief softens and compresses while laser energy is applied.

2. The method of claim 1, wherein applying laser energy further comprises rotating the breakaway hub and catheter shaft while applying laser energy.

3. The method of claim 2, further comprising translating the breakaway hub and catheter shaft while applying laser energy.

4. The method of claim 1, further comprising monitoring a temperature of a surface upon which laser energy is incident upon in order to control operation of the laser.

5. The method of claim 4, wherein monitoring the temperature of the surface includes applying laser energy via an infrared feedback laser.

6. The method of claim 1, wherein applying heat to shrink the strain relief sleeve comprises subjecting the strain relief sleeve to heated air.

7. The method of claim 1, wherein the breakaway hub comprises a styrene-butadiene copolymer.

8. The method of claim 1, wherein the catheter shaft comprises a polyether block amide having a Shore hardness of about 72D.

9. The method of claim 1, wherein the retainer sleeve comprises a polyether block amide having a Shore hardness of about 55D to about 63D.

10. The method of claim 1, wherein the strain relief sleeve comprises a coextruded tube having a heat-flowable polyether block amide inner layer and a cross-linked polyether block amide outer layer.

11. A method of attaching a hub to a catheter shaft, the hub having a proximally extending shaft portion and one or more bosses projecting from the proximally extending shaft portion, the catheter shaft including a proximal portion, the method comprising steps of:
    inserting the catheter shaft into the hub such that the proximally extending shaft portion extends over the proximal portion of the catheter shaft;
    disposing a retainer sleeve over the proximally extending shaft portion, the retainer sleeve including a slit configured to accommodate the one or more bosses therethrough;
    shrinking a strain relief sleeve over the retainer sleeve;
    shrinking a heat shrink tube over the strain relief sleeve;
    rotating and translating the hub and catheter shaft while subjecting a portion of the hub to laser energy to secure the hub to the proximal portion of the catheter shaft; and
    removing the heat shrink tube;
    wherein the at least one boss projecting from the proximally extending shaft portion softens and compresses while laser energy is applied.

12. The method of claim 11, further comprising monitoring a temperature of a surface upon which laser energy is incident upon in order to control operation of the laser.

13. The method of claim 12, wherein monitoring the temperature of the surface includes applying laser energy via an infrared feedback laser.

14. The method of claim 11, wherein the hub comprises a styrene-butadiene copolymer.

15. The method of claim 11, wherein the catheter shaft comprises a polyether block amide.

16. The method of claim 11, wherein the retainer sleeve comprises a polyether block amide having a lower durometer value than that of the catheter shaft.

17. The method of claim 11, wherein the strain relief sleeve comprises a coextruded tube having a heat-flowable inner layer and a cross-linked outer layer.

* * * * *